US008202267B2

(12) United States Patent
Field et al.

(10) Patent No.: US 8,202,267 B2
(45) Date of Patent: Jun. 19, 2012

(54) METHOD AND APPARATUS FOR INFUSING LIQUID TO A BODY (75) Inventors: Jeffrey F. Field, Camarillo, CA (US); April A. Marano-Ford, Manhattan Beach, CA (US); Peter R. Rule, Los Altos Hills, CA (US); Kevin J. O'Hara, Evergreen, CO (US); Thomas Allen Knotts, Mountain View, CA (US)

(73) Assignee: Medsolve Technologies, Inc., Manhattan Beach, CA (US)

( * ) Notice: Subject to any disclaimer, the term of this patent is extended or adjusted under 35 U.S.C. 154(b) by 1348 days.

(21) Appl. No.: 11/548,238

(22) Filed: Oct. 10, 2006

(65) Prior Publication Data

US 2008/0086086 A1 Apr. 10, 2008

(51) Int. Cl.
*A61K 9/22* (2006.01)
*A61M 37/00* (2006.01)
*G05D 11/00* (2006.01)

(52) U.S. Cl. .................... 604/890.1; 604/93.01; 700/282

(58) Field of Classification Search ............... 604/890.1, 604/67, 131, 123, 65, 93.01; 700/282
See application file for complete search history.

(56) References Cited

U.S. PATENT DOCUMENTS 4,221,219 A 9/1980 Tucker .......................... 128/260
(Continued)

FOREIGN PATENT DOCUMENTS

EP 1 837 787 9/2007

OTHER PUBLICATIONS

PCT Application No. PCT/US2007/80853 filed Oct. 9, 2007.
(Continued)

*Primary Examiner* — Jackie Ho
*Assistant Examiner* — Weng Lee
(74) *Attorney, Agent, or Firm* — Connolly Bove Lodge & Hutz LLP (57) ABSTRACT

A system for infusing liquid to a body includes an infusion device, a network interface with a cell phone and wireless link and a network server system capable of communication with the infusion device through the network interface. The server system has access to a file of information specific to the controller for the infusion device. The infusion device includes a source of infusion fluid, a delivery port, a pump between the source of infusion fluid and the delivery port and a controller capable of programmable pump rate and sequence. A method for infusing liquid to a body includes controlling infusion using a programmable controller, establishing a file of information specific to the controller accessible to an extended area network server system and remotely transmitting commands to the controller. The information specific to the controller in the file is amended from a control terminal remote from the body. Operating instructions responsive to the updated information in the file are provided over an extended area network to a programmable two-way communication device. The device is capable of communication with the controller to forward operating commands. Requests for a bolus or a basal rate change are made through input to the two-way communication device which responds with commands transmitted over the wireless link to the controller consistent with the operating instructions from the server system. Network access through a monitoring terminal to the incidents of amending information specific to the controller is used for generating payments for the incidents of amending information specific to the controller accessed by the monitoring terminal.

9 Claims, 7 Drawing Sheets

U.S. PATENT DOCUMENTS

| | | | |
|---|---|---|---|
| 4,231,019 A | 10/1980 | Junginger et al. | 340/171 R |
| 4,373,527 A | 2/1983 | Fischell | 128/260 |
| 4,449,893 A | 5/1984 | Beckman et al. | 417/322 |
| 4,468,221 A | 8/1984 | Mayfield | 604/152 |
| 4,469,481 A | 9/1984 | Kobayashi | 604/67 |
| 4,565,542 A | 1/1986 | Berg | 604/131 |
| 4,596,575 A | 6/1986 | Rosenberg et al. | 604/891 |
| 4,650,469 A | 3/1987 | Berg et al. | 604/131 |
| 4,685,903 A | 8/1987 | Cable et al. | 604/154 |
| 4,734,092 A | 3/1988 | Millerd | 604/67 |
| 4,871,351 A | 10/1989 | Feingold | 604/66 |
| 4,886,499 A | 12/1989 | Cirelli et al. | 604/131 |
| 4,898,578 A | 2/1990 | Rubalcaba, Jr. | 604/66 |
| 4,944,659 A | 7/1990 | Labbe et al. | 417/413.2 |
| 5,085,562 A | 2/1992 | van Lintel | 417/413.2 |
| 5,205,819 A | 4/1993 | Ross et al. | 604/67 |
| 5,219,278 A | 6/1993 | van Lintel | 417/413.1 |
| 5,224,843 A | 7/1993 | van Lintel | 417/413.2 |
| 5,271,724 A | 12/1993 | van Lintel | 417/413.2 |
| 5,277,556 A | 1/1994 | van Lintel | 417/413.2 |
| 5,328,460 A | 7/1994 | Lord et al. | 604/67 |
| 5,338,157 A | 8/1994 | Blomquist | 417/2 |
| 5,376,070 A | 12/1994 | Purvis | 604/31 |
| 5,433,710 A | 7/1995 | Van Antwerp | 604/152 |
| 5,443,508 A | 8/1995 | Giampapa | 623/11 |
| 5,480,386 A | 1/1996 | Brohy et al. | 604/131 |
| 5,485,408 A | 1/1996 | Blomquist | 364/578 |
| 5,507,737 A | 4/1996 | Palmskog | 604/891.1 |
| 5,569,186 A | 10/1996 | Lord et al. | 604/67 |
| 5,569,187 A | 10/1996 | Kaiser | 604/67 |
| 5,575,770 A | 11/1996 | Melsky et al. | 604/93 |
| 5,582,593 A | 12/1996 | Hultman | 604/65 |
| 5,630,710 A | 5/1997 | Tune et al. | 417/326 |
| 5,637,095 A | 6/1997 | Nason et al. | 604/135 |
| 5,658,250 A | 8/1997 | Blomquist et al. | 604/65 |
| 5,665,070 A | 9/1997 | McPhee | 604/131 |
| 5,695,473 A | 12/1997 | Olsen | 604/153 |
| 5,707,361 A | 1/1998 | Slettenmark | 604/131 |
| 5,725,363 A | 3/1998 | Bustgens et al. | 417/413.1 |
| 5,759,014 A | 6/1998 | Van Lintel | 417/413.3 |
| 5,759,015 A | 6/1998 | Van Lintel et al. | 417/322 |
| 5,761,782 A | 6/1998 | Sager | 29/25.35 |
| 5,764,159 A | 6/1998 | Neftel | 340/870.09 |
| 5,773,913 A | 6/1998 | Casselden | 310/338 |
| 5,788,669 A | 8/1998 | Peterson | 604/67 |
| 5,798,600 A | 8/1998 | Sager et al. | 310/330 |
| 5,807,375 A | 9/1998 | Gross et al. | 604/890.1 |
| 5,810,015 A | 9/1998 | Flaherty | 128/899 |
| 5,848,991 A | 12/1998 | Gross et al. | 604/140 |
| 5,858,005 A | 1/1999 | Kriesel | 604/180 |
| 5,931,814 A | 8/1999 | Alex et al. | 604/131 |
| 5,935,099 A | 8/1999 | Peterson et al. | 604/65 |
| 5,954,058 A | 9/1999 | Flaherty | 128/899 |
| 5,957,890 A | 9/1999 | Mann et al. | 604/131 |
| 5,957,895 A | 9/1999 | Sage et al. | 604/181 |
| 5,961,492 A | 10/1999 | Kriesel et al. | 604/32 |
| 5,997,263 A | 12/1999 | Van Lintel et al. | 417/413.2 |
| 5,997,501 A | 12/1999 | Gross et al. | 604/65 |
| 6,106,498 A | 8/2000 | Friedli et al. | 604/153 |
| 6,174,300 B1 | 1/2001 | Kriesel et al. | 604/132 |
| 6,237,619 B1 | 5/2001 | Maillefer et al. | 137/15.18 |
| 6,248,093 B1 | 6/2001 | Moberg | 604/131 |
| 6,259,587 B1 | 7/2001 | Sheldon et al. | 361/23 |
| 6,309,189 B1 | 10/2001 | Rey-Mermet et al. | 417/413.3 |
| 6,375,638 B2 | 4/2002 | Nason et al. | 604/132 |
| 6,390,791 B1 | 5/2002 | Maillefer et al. | 417/413.3 |
| 6,423,035 B1 | 7/2002 | Das et al. | 604/155 |
| 6,458,102 B1 | 10/2002 | Mann et al. | 604/131 |
| 6,461,331 B1 | 10/2002 | Van Antwerp | 604/131 |
| 6,485,461 B1 | 11/2002 | Mason et al. | 604/132 |
| 6,488,652 B1 | 12/2002 | Weijand et al. | 604/93.01 |
| 6,585,695 B1 | 7/2003 | Adair et al. | 604/183 |
| 6,589,229 B1 * | 7/2003 | Connelly et al. | 604/890.1 |
| 6,589,299 B2 | 7/2003 | Missling et al. | 29/623.5 |
| 6,595,756 B2 | 7/2003 | Gray et al. | 417/44.1 |
| 6,645,142 B2 | 11/2003 | Braig et al. | 600/300 |
| 6,656,148 B2 | 12/2003 | Das et al. | 604/67 |
| 6,656,158 B2 | 12/2003 | Mahoney et al. | 604/131 |
| 6,656,159 B2 | 12/2003 | Flaherty | 604/131 |
| 6,669,669 B2 | 12/2003 | Flaherty et al. | 604/132 |
| 6,692,457 B2 | 2/2004 | Flaherty | 604/67 |
| 6,699,218 B2 | 3/2004 | Flaherty et al. | 604/131 |
| 6,716,002 B2 | 4/2004 | Higashino | 417/413.2 |
| 6,719,739 B2 | 4/2004 | Verbeek et al. | 604/288.04 |
| 6,723,072 B2 | 4/2004 | Flaherty et al. | 604/131 |
| 6,740,059 B2 | 5/2004 | Flaherty | 604/67 |
| 6,740,072 B2 | 5/2004 | Starkweather et al. | 604/504 |
| 6,749,587 B2 * | 6/2004 | Flaherty | 604/151 |
| 6,752,787 B1 | 6/2004 | Causey et al. | 604/131 |
| 6,768,425 B2 | 7/2004 | Flaherty et al. | 340/870.07 |
| 6,770,067 B2 | 8/2004 | Lorenzen et al. | 604/891.1 |
| 6,774,437 B2 | 8/2004 | Bryant et al. | 257/350 |
| 6,809,653 B1 | 10/2004 | Mann et al. | 340/870.28 |
| 6,827,559 B2 * | 12/2004 | Peters et al. | 417/413.2 |
| 6,827,702 B2 | 12/2004 | Libel et al. | 604/67 |
| 6,830,558 B2 | 12/2004 | Flaherty et al. | 604/67 |
| 6,843,782 B2 | 1/2005 | Gross et al. | 604/141 |
| 6,852,104 B2 | 2/2005 | Blomquist | 604/504 |
| 6,878,132 B2 | 4/2005 | Kipfer | 604/111 |
| 6,948,918 B2 | 9/2005 | Hansen | 417/395 |
| 6,960,192 B1 | 11/2005 | Flaherty et al. | 604/181 |
| 6,974,437 B2 | 12/2005 | Lebel et al. | 604/65 |
| 6,986,649 B2 | 1/2006 | Dai et al. | 417/413.2 |
| 6,997,921 B2 * | 2/2006 | Gray et al. | 604/891.1 |
| 7,005,078 B2 | 2/2006 | Van Lintel et al. | 604/504 |
| 7,018,360 B2 | 3/2006 | Flaherty et al. | 604/123 |
| 7,052,251 B2 | 5/2006 | Nason et al. | 417/321 |
| 7,107,086 B2 | 9/2006 | Reihl et al. | 600/310 |
| 7,115,111 B2 | 10/2006 | Haindl | 604/158 |
| 7,122,005 B2 | 10/2006 | Shusterman | 600/300 |
| 7,128,727 B2 | 10/2006 | Flaherty et al. | 604/131 |
| 7,128,730 B2 | 10/2006 | Marano-Ford et al. | 604/167.05 |
| 7,137,964 B2 | 11/2006 | Flahery | 604/67 |
| 7,141,023 B2 | 11/2006 | Diermann et al. | 600/573 |
| 7,144,384 B2 | 12/2006 | Gorman et al. | 604/131 |
| 7,179,226 B2 | 2/2007 | Crothall et al. | 600/300 |
| 7,186,236 B2 | 3/2007 | Gibson et al. | 604/93.01 |
| 7,193,521 B2 | 3/2007 | Moberg et al. | 340/679 |
| 7,195,609 B2 | 3/2007 | Huegli | 604/67 |
| 7,204,823 B2 | 4/2007 | Estes et al. | 604/65 |
| 7,218,968 B2 | 5/2007 | Condie et al. | 607/59 |
| 7,255,690 B2 | 8/2007 | Gray et al. | 604/891.1 |
| 7,258,253 B2 | 8/2007 | Nicol et al. | 222/420 |
| 7,268,466 B2 | 9/2007 | Rasmussen | 310/328 |
| 7,275,522 B2 | 10/2007 | Beilharz et al. | 123/490 |
| 7,284,474 B2 * | 10/2007 | Eigemann et al. | 92/168 |
| 7,284,962 B2 | 10/2007 | Blakey | 417/53 |
| 7,287,965 B2 | 10/2007 | Vogeley et al. | 417/413.2 |
| 7,290,993 B2 | 11/2007 | Vogeley et al. | 417/413.2 |
| 7,291,107 B2 | 11/2007 | Hellwig et al. | 600/365 |
| 7,297,111 B2 | 11/2007 | Iliff | 600/300 |
| 7,300,402 B2 | 11/2007 | Iliff | 600/300 |
| 7,303,549 B2 | 12/2007 | Flaherty et al. | 604/181 |
| 7,306,560 B2 | 12/2007 | Iliff | 600/300 |
| 2002/0029776 A1 | 3/2002 | Blomquist | 128/200.11 |
| 2002/0040208 A1 | 4/2002 | Flaherty et al. | |
| 2002/0072733 A1 | 6/2002 | Flaherty | 604/890.1 |
| 2003/0014011 A1 | 1/2003 | Robert | |
| 2003/0032867 A1 | 2/2003 | Crothall | 600/300 |
| 2003/0050626 A1 | 3/2003 | Gibson et al. | |
| 2003/0055380 A1 | 3/2003 | Flaherty | 604/155 |
| 2003/0163088 A1 | 8/2003 | Blomquist | 604/131 |
| 2004/0078028 A1 | 4/2004 | Flaherty et al. | 604/892.1 |
| 2004/0092873 A1 | 5/2004 | Moberg | |
| 2004/0116866 A1 | 6/2004 | Gorman et al. | |
| 2004/0158230 A1 | 8/2004 | Hunn et al. | 604/523 |
| 2004/0204673 A1 | 10/2004 | Flaherty | |
| 2004/0220551 A1 | 11/2004 | Flaherty et al. | 604/890.1 |
| 2004/0235446 A1 | 11/2004 | Flaherty et al. | |
| 2004/0260233 A1 | 12/2004 | Garibotto et al. | |
| 2005/0022274 A1 | 1/2005 | Campbell et al. | 604/131 |
| 2005/0043676 A1 | 2/2005 | Remde et al. | |
| 2005/0065464 A1 | 3/2005 | Talbot et al. | 604/66 |
| 2005/0065760 A1 | 3/2005 | Murtfeldt et al. | 703/11 |
| 2005/0090808 A1 | 4/2005 | Malave et al. | 604/890.1 |
| 2005/0137573 A1 | 6/2005 | McLaughlin | 604/504 |
| 2005/0159708 A1 | 7/2005 | Sidler | |

| | | |
|---|---|---|
| 2005/0171512 A1 | 8/2005 | Flaherty |
| 2005/0177137 A1 | 8/2005 | Kipfer |
| 2005/0182366 A1 | 8/2005 | Vogt et al. .................. 604/131 |
| 2005/0182391 A1 | 8/2005 | Schiltges et al. |
| 2005/0197625 A1 | 9/2005 | Haueter et al. |
| 2005/0215982 A1 | 9/2005 | Malave et al. ............ 604/890.1 |
| 2005/0222645 A1 | 10/2005 | Malave et al. ................. 607/60 |
| 2005/0238507 A1 | 10/2005 | DiIanne et al. .............. 417/415 |
| 2005/0273080 A1 | 12/2005 | Paul |
| 2006/0031094 A1 | 2/2006 | Cohen et al. |
| 2006/0036134 A1 | 2/2006 | Tarassenko et al. .......... 600/300 |
| 2006/0041229 A1 | 2/2006 | Garibotto et al. ............. 604/122 |
| 2006/0047192 A1 | 3/2006 | Hellwig et al. |
| 2006/0047538 A1 | 3/2006 | Condurso et al. ................ 705/3 |
| 2006/0074381 A1 | 4/2006 | Malave et al. ............ 604/93.01 |
| 2006/0116664 A1 | 6/2006 | Richter et al. |
| 2006/0137695 A1 | 6/2006 | Hellwig et al. |
| 2006/0178633 A1 | 8/2006 | Garibotto et al. ............. 604/155 |
| 2006/0282290 A1 | 12/2006 | Flaherty et al. ................... 705/2 |
| 2007/0118405 A1 | 5/2007 | Campbell et al. ................. 705/2 |
| 2007/0129688 A1 | 6/2007 | Scheurer et al. .............. 604/263 |
| 2007/0166181 A1* | 7/2007 | Nilson .......................... 417/478 |
| 2007/0181425 A1 | 8/2007 | Kim .......................... 204/403.11 |
| 2007/0219480 A1 | 9/2007 | Kamen et al. ................... 604/20 |
| 2007/0233206 A1 | 10/2007 | Frikart et al. .................... 607/60 |
| 2007/0251835 A1 | 11/2007 | Mehta et al. .................. 205/783 |
| 2007/0253021 A1 | 11/2007 | Mehta .......................... 358/1.15 |
| 2007/0253380 A1 | 11/2007 | Jollota et al. .................. 370/338 |
| 2007/0254593 A1 | 11/2007 | Jollota et al. ............... 455/67.11 |
| 2007/0255116 A1 | 11/2007 | Mehta et al. .................. 600/300 |
| 2007/0255126 A1 | 11/2007 | Moberg et al. ................. 600/365 |
| 2007/0255250 A1 | 11/2007 | Moberg et al. ................. 604/503 |
| 2007/0255348 A1 | 11/2007 | Holtzclar ........................ 607/60 |
| 2007/0258395 A1 | 11/2007 | Jollota et al. .................. 370/310 |
| 2008/0119705 A1 | 5/2008 | Patel et al. ..................... 600/347 |

OTHER PUBLICATIONS

Office Action mailed Jan. 8, 2009 in U.S. Appl. No. 11/618,682, filed Dec. 29, 2006.
Amendment filed Apr. 8, 2009 in response to OA mailed Jan. 8, 2009 in U.S. Appl. No. 11/618,682, filed Dec. 29, 2006.
Office Action mailed Jul. 8, 2009 in U.S. Appl. No. 11/618,682, filed Dec. 29, 2006.
Amendment After Final Official Action filed Sep. 8, 2009 in response to OA mailed Jul. 8, 2009 in U.S. Appl. No. 11/618,682, filed Dec. 29, 2006.
Express Abandonment filed Sep. 29, 2009 in U.S. Appl. No. 11/618,682, filed Dec. 29, 2006.
Advisory Action Before the Filing of an Appeal Brief mailed Oct. 5, 2009 in U.S. Appl. No. 11/618,682, filed Dec. 29, 2006.
Notice of Abandonment mailed Oct. 8, 2009 in U.S. Appl. No. 11/618,682, filed Dec. 29, 2006.
PCT Application No. PCT/US2007/86835 filed Dec. 7, 2007.
U.S. Appl. No. 11/618,682, filed Dec. 29, 2006.
U.S. Appl. No. 12/021,164, filed Jan. 28, 2008.
Official Action mailed Jan. 8, 2009 in companion U.S. Appl. No. 11/618,682, filed Dec. 29, 2006.

* cited by examiner

METHOD AND APPARATUS FOR INFUSING LIQUID TO A BODY

BACKGROUND OF THE INVENTION

The field of the present invention is infusion control systems.

Today, diabetes is understood to be reaching epidemic proportions in the United States. It remains as a worldwide problem as well. Diabetes brings with it a host of medical problems which are aggravated by conventional medicament dosage schemes. Traditional shots and the like are intermittent which can induce a cyclical plethora and paucity of medicament, typically insulin. Recent efforts have been undertaken to eliminate such harmful cyclical variations through continuous administration of medicament. Additionally, devices and controls have been designed to provide both a basal rate for sustained infusion and periodic boluses to accommodate the ingestion of carbohydrates. In spite of these advantageous capabilities, difficulties remain in accommodating the correct infusion regiment, clinician control and payer's oversight.

A wide variety of prior systems having applicable components and processes exist. Reference is made to U.S. Pat. Nos. 4,898,578; 5,205,819; 5,630,710; 6,852,104; and 7,018,360. Reference is also made to U.S. Patent Publications Nos. 2002/0029776; 2003/0032867; 2003/0163088; 2004/0220551; and 2005/0137573. The disclosures of the foregoing patents and patent publications are incorporated herein by reference.

In addition to the infusion of insulin for diabetes, infusion is useful for other purposes in bodies of both humans and animals. The types of liquids that can be delivered include, but are not limited to, insulin, antibiotics, nutritional fluids, total parenteral nutrition or TPN, analgestics, morphine, hormones or hormonal drugs, gene therapy drugs, anticoagulants, analgesics, cardiovascular medications, AZT and chemotherapeutics. The types of medical conditions treatable by infusion include, but are not limited to, diabetes, cardiovascular disease, pain, chronic pain, cancer, AIDS, neurological diseases, Alzheimer's Disease, ALS, Hepatitis, Parkinson's Disease or spasticity.

SUMMARY OF THE INVENTION

The present invention is directed to method and apparatus for infusing liquid to a body. Both contemplate the employment of an infusion device including a controller capable of programmable rate and time sequences. A separate programmable device is employed in the infusion system.

In a first separate aspect of the present invention, an infusion system includes the infusion device and a two-way communication device communicating with the controller through electrical contacts or a wireless link. A server system capable of communication with the two-way communication device through an extended area network has access to a file of information specific to the controller. The server system may also be capable of association with multiple two-way communication devices cooperating with multiple infusion devices.

In a second separate aspect of the present invention, an infusion system again includes the infusion device and a two-way communication device. A server system capable of communication with the two-way communication device has access to a file of information specific to the controller. The server system further includes at least one of a control terminal capable of inputting and changing the information specific to the controller in the file or a monitoring terminal capable of monitoring the inputting and changing of such operating instructions. Extended area network access for either of the control terminal and the monitoring terminal is also contemplated.

In a third separate aspect of the present invention, an infusion system again includes the infusion device and a two-way communication device. A server system capable of communication with the two-way communication device has access to a file of information specific to the controller. A wireless link incorporates a radio chip at the controller using a local area communication standard. The two-way communication device is capable of communicating with the radio chip. Such local area communication standards which may be employed are Bluetooth® NFC or Wibree™.

In a fourth separate aspect of the present invention, an infusion system again includes the infusion device and a two-way communication device. A server system capable of communication with the two-way communication device has access to a file of information specific to the controller. A wireless link incorporates a radio chip at the controller using a local area communication standard. The two-way communication device is capable of communicating with the radio chip using the local area communication standard. The two-way communication device employs one or both of voice and text communication.

In a fifth separate aspect of the present invention, an infusion system again includes the infusion device and a two-way communication device. A server system has access to a file of information specific to the controller. The two-way communication device is capable of communicating with the controller and the server system and is programmable by the server system over an extended area network. The network access may be through a wireless network link such as a cellular network, a wide area network or a combination of the two. Text messaging as well as voice communications are contemplated.

In a sixth separate aspect of the present invention, an infusion system again includes the infusion device and a two-way communication device. A server system capable of communication with the two-way communication device has access to a file of information specific to the controller. The infusion system further includes a sensor for generating a diagnostic signal. The sensor is in communication with either the controller or the two-way communication device for incorporation of the diagnostic signal into commands for operation of the controller.

In a seventh separate aspect of the present invention, an infusion system again includes the infusion device having a source of infusion fluid, a delivery port, a metering element and the controller capable of programmable infusion rate and time sequences. A programmable cell phone or PDA capable of two-way communication with the controller is used to control the infusion device.

In an eighth separate aspect of the present invention, an infusion device has a single use disposable assembly including a source of infusion fluid, a delivery port, a pump with a pump chamber and a movable pumping element. A multiuse assembly engageable with the single use disposable assembly has a pump driver extending to the movable pumping element and a controller capable of programmable infusion rate and time sequences. The disposable assembly and the multiuse assembly may each have a housing with an engagement and the pump driver has an actuator member extending to operatively engage the movable pumping element.

In a ninth separate aspect of the present invention, a method of infusing liquid to a body includes regulating infusion to the body using a programmable controller. A file of information specific to the controller is established and accessed by a network server system for transmitting operating instructions to a two-way communication device through an extended area network. The method further contemplates amending the information specific to the controller from a control terminal remote from the body. Requests for a bolus, a basal rate or other changes are input to the two-way communication device.

In a tenth separate aspect of the present invention, a method for infusing liquid to a body contemplates controlling infusion to the body using a programmable controller, establishing a file of information specific to the controller for transmitting commands from a network server through an extended area network to a two-way communication device. The method further contemplates amending operating instructions specific to the controller in the file from a control terminal remote from the body and providing network access through a monitoring terminal to monitor the incidents of amending operating instructions. Such monitoring can enable generation of payments to clinicians for the incidents of amending operating instructions.

In a eleventh separate aspect of the present invention, a method of infusing liquid to a body includes regulating infusion to the body using a programmable controller. A file of information specific to the controller is established and accessed by a network server system for transmitting operating instructions to a two-way communication device through a extended area network. The two-way communication device transmits commands to the controller through a local area wireless network interface. The method further contemplates amending the information specific to the controller from a control terminal remote from the body. A request for a bolus, a basal rate change or other input may be made to the two-way communication device. Commands are then transmitted to the controller responsive to the request. Data indicative of the magnitude of a constituent of liquid in the body is input to the server system.

In a twelfth separate aspect of the present invention, a method of infusing liquid to a body includes regulating infusion to the body using a programmable controller. A file of information specific to the controller is established and accessed by a network server system for transmitting operating instructions to a two-way communication device. The method further contemplates amending the operating instructions specific to the controller from a control terminal remote from the body and also contemplates inputting a request for a bolus or a basal rate change through the two-way communication device. Commands are transmitted from the two-way communication device to the controller responsive to the request for a bolus or a basal rate change. Transmitted operating instructions from the server system to the two-way communication device govern the commands response to input of a request for a bolus or basal rate change. The two-way communication device may be to a cellular telephone or a hand held computer with wireless data link and may include text messaging, voice communication or keypad input.

In a thirteenth separate aspect of the present invention, any of the foregoing aspects are contemplated to be combined to further advantage.

Accordingly, it is an object of the present invention to provide improved method and apparatus for the infusing of liquid to a body. Other and further objects and advantages will appear hereinafter.

DETAILED DESCRIPTION OF THE PREFERRED EMBODIMENT

Figure 1:
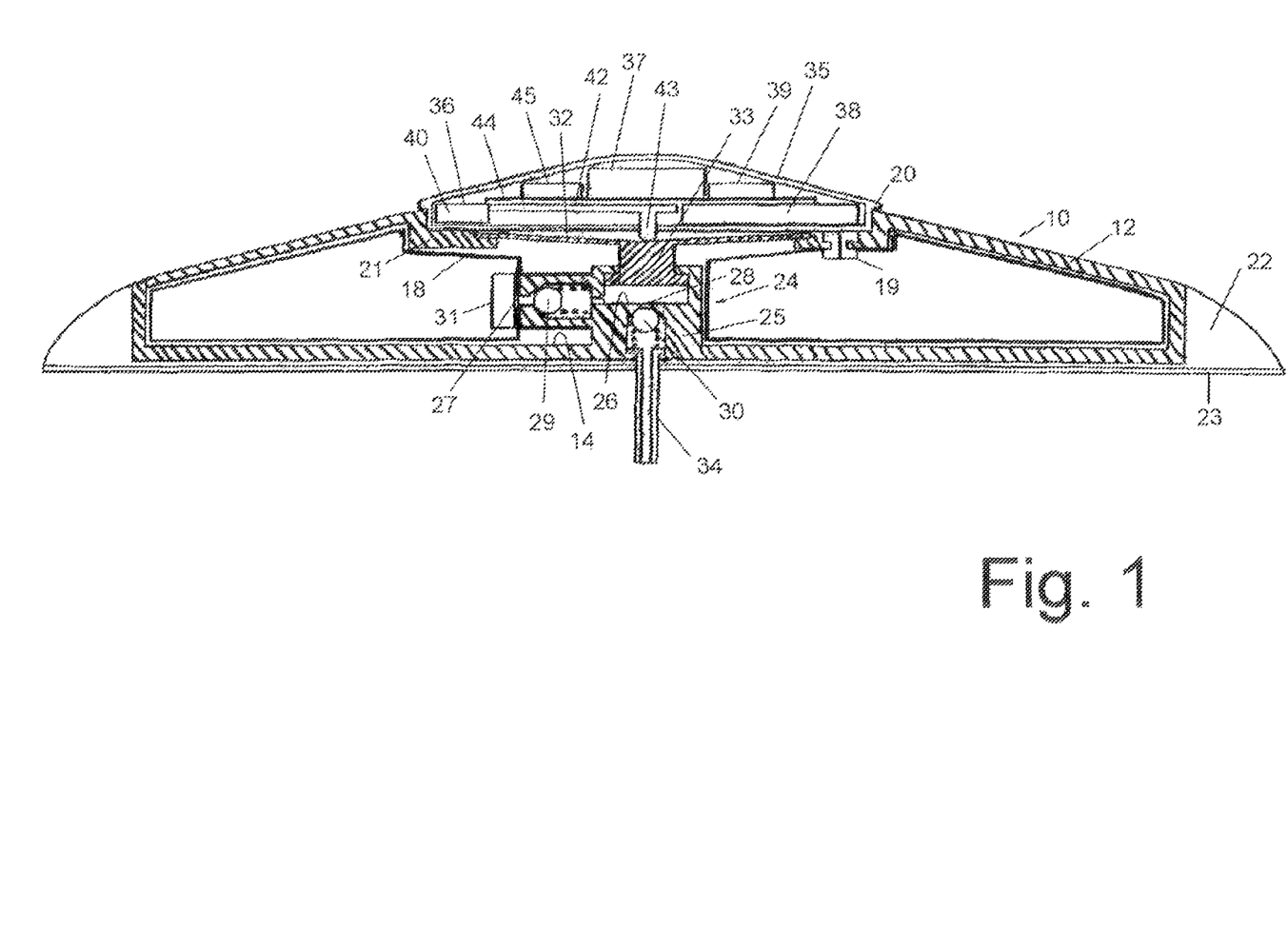
FIG. 1 is a cross-sectional side view of an infusion device.

Turning in detail to a preferred embodiment of a system for infusing liquid to a body, an infusion device, generally designated 10, includes a housing 12 conveniently circular in plan with a preferably low profile and a flat base. Shapes other than circular are also possible and the base may have some concavity for conformance to a body shape. With a circular shape, the housing 12 most conveniently defines an annular space 14 for a reservoir to provide a source of infusion fluid. The reservoir may be defined by the annular space 14 or may include an internal annular bladder 18 of PTFE or nonplasticized PVC with an elastomeric fill port 19. A circular opening 20 is centrally located in the top of the housing 12 with a recessed mounting flange 12 further includes an elastomeric overmold periphery and mounting surface 22 for soft edges and comfort. The infusion device 10 is intended to be placed on the skin of the body to be infused and held in place by such means as an adhesive coating 23, tape or other medical retaining system.

A metering element is provided in the housing 12. In the preferred embodiment, the metering element is a pump, generally designated 24. Other possibilities for the metering element include a valve to vent pressurized liquid or a single stroke piston dispensing through a restricted orifice. A central boss 25 concentrically located within the housing 12 defines a pump body with a pump chamber 26, an inlet 27 and an outlet 28. The pump formed thereby is conveniently centrally located within the housing 12 in this preferred embodiment. The pump includes two one-way valves 29, 30 each defined by a ball biased against a seat by a coil spring. A filter 31, which passes liquid but blocks gas, is located at the inlet 27.

A circular diaphragm 32 is shown extending across the central opening 20 of the housing 12 attached to the circular recessed mounting flange 21. The diaphragm 32 is resilient, being of elastomeric material and includes a centrally positioned integral piston 33. The piston 33, operating as a movable pumping element, extends to the pump chamber 26 formed in the central boss 25 to vary the chamber volume. The diaphragm 32 is in radial tension to create a restoring force to maintain the piston biased toward one end of its stroke in the pump chamber 26.

The housing 12, with the bladder 18, the pump 24 and a delivery port to the body defined by a rigid cannula 34, is considered disposable and is fabricated in an inexpensive manner. The delivery port 34 to the body contemplates single use. The capacity of the reservoir is intended to exceed the demand for medicament during the full term of use which may be some multiple of a twenty four hour period depending on the expected volume of use.

The infusion device 10 further includes a second housing 35 which is not considered disposable at the same rate as the housing 12 and has multiuse capability with a plurality of disposable housings 12. The second housing 35 is placed in the circular opening 20 and can be secured by an interference fit, interlocking flanges or a threaded engagement to define an engagement. The second housing 35 includes a pump driver 36, a pump controller 37 and a battery 38.

The pump driver 36 includes a mounting block 40 that retains an actuator arm 42 which is a laminated strip with one spring leaf and a piezoelectric strip that deforms the arm 42 when voltage is applied. An actuator member 43 at the end of the arm 42 extends from the arm 42 through the housing 35 to operatively engage the piston 33 of the diaphragm 32. The driver 36 acts in one direction to force the piston 33 into the pump chamber 26 while the tension in the diaphragm 32 drives the return stroke. Other drives include a screw oscillating about its axis to advance the piston using a nanomotor or magnetic contacts to drive the oscillations.

The battery 38 may be a conventional watch battery. Alternatively, a rechargeable battery may be employed which can be recharged by an induction charger or by more conventional means. The battery 38 powers the driver 36 through the controller 37.

The controller 37 is electronic and is programmable for delivering a range of infusion rates and timing of the sequences of actuation with a capability to oscillate power delivery from the battery 38 to the pump driver 36. Through this programming, a basal rate can be controlled as well as periodic boluses. The controller 37 also can provide device ID and monitor such parameters as battery life. Alarm modes and volume, timing of communication and other infusion device functions can be added to the function of the controller 37. Being programmable, a microcontroller with memory is integrated on a circuit board 44. Other elements included on the board(s) 44 as needed or advantageous include a battery monitoring circuit, a power switch, a DC/DC converter, a voltage regulator, an LED and driver, an alarm generator, a jack or antenna, an induction coil and a crystal reference with the microcontroller.

The controller 37 includes a wireless link 39 for communication to and from the controller 37 using a radio chip on the circuit board 44 to transceive commands to the controller and unit identify and device status from the controller 37. The radio chip 39 uses a local area communication standard. Bluetooth®, NFC and Wibree™ communication standards can be used, with NFC requiring greater proximity of the components for communication.

Figure 2:
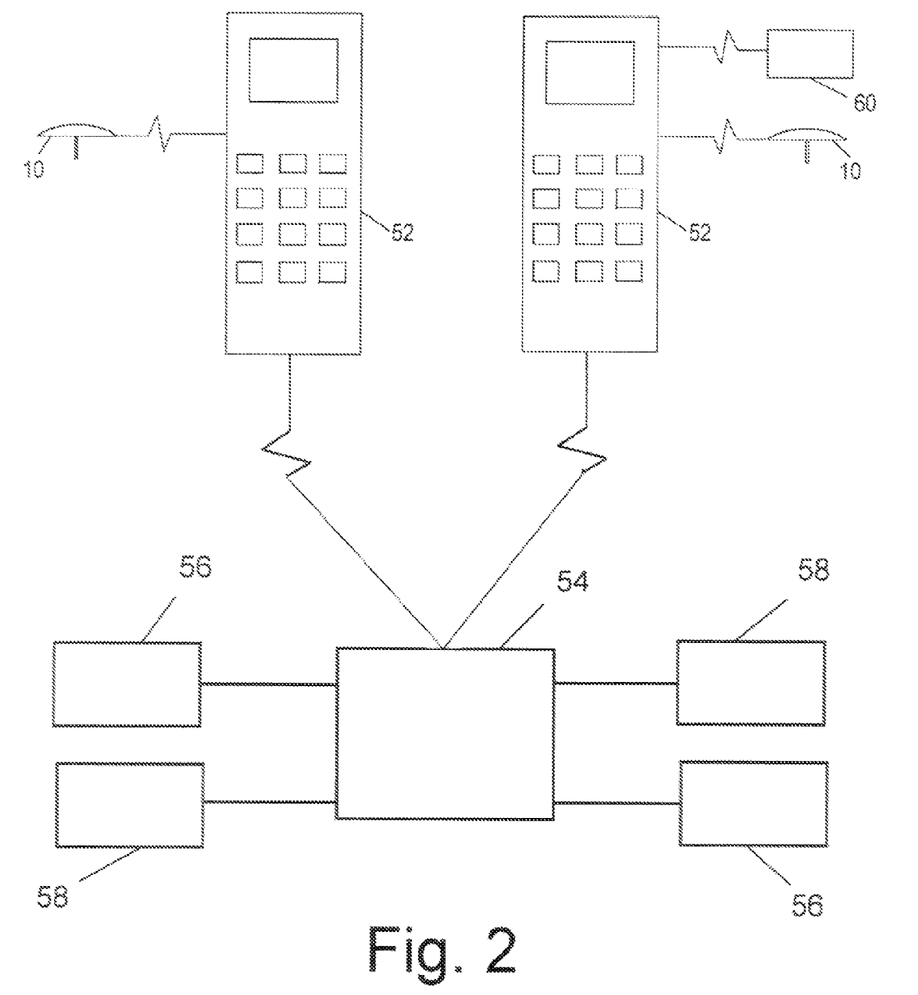
FIG. 2 is schematic view of a network system.

A programmable multi-function device capable of two-way communication with the controller 37 and separate from the infusion device 10 is employed for communication to the wireless link 39 using the local area communication standard. This device, as a two-way communication device 52, is in turn in communication with an extended area network. In the preferred embodiment, the two-way communication device 52 is a cellular telephone preferably with Java-enabled program capability. A hand held computer with a wireless data link such as a BlackBerry®, a Treo™ or other similar device, with the computer portion often identified as a "PDA", is also contemplated. The phrase "two-way communication device" is intended to include all such possibilities while the terms "cellular phone" and its variations and the term "PDA" are intended to include those devices which access a public network for communication and data transfer. Such devices can advantageously download selected programs from the internet as may be used for glucose monitoring using a sensor or the like.

The extended area network with which the two-way communication device 52 is communicating may, therefore, be a cellular telephone network, a wide area network such as the internet or a private wide area network or a combination of technologies as systems become more integrated and the phrase "extended area network" is intended to include all such possibilities.

In a preferred embodiment, the protocol is through text communication, however, as, for example, diabetics can have vision problems as a symptom of that disease, voice communication to the two-way communication device 52 from the extended area network may be preferred. Response through the extended area network by cell phone keypad or voice would also be possible.

A server system 54 compatible with the extended area network is in selective communication with the two-way communication device 52 through the extended area network. This system 54 has access to a file of information specific to the controller 37. When connected through the extended area network, the server system 54 can provide operating instructions to the two-way communication device 52 for programming the controller 37 for infusion rate and timing sequences. The server system 54 may be employed to communicate in real time with the controller 37 through the extended area network and the wireless link 39 by relaying commands through the two-way communication device but more facilely can download programming and data to the programmable two-way communication device 52 for later and/or repeated communication with the controller 37.

The file of information specific to the controller accessible by the server system is accessible for creating and amending instructions from a control terminal 56. The control terminal is accessible by a clinician for inputting and changing the file through network access.

A monitoring terminal 58 can also be employed. The monitoring terminal 58 has limited access to the file of information specific to the controller. The terminal is intended to be employed by payers to service providers, e.g., medical insurance companies. The payer is anticipated to be interested in at least the incidents of inputting and changing of the file of information specific to the controller by the clinician. Additionally, the payer may be set to see the results of clinician control for purposes of evaluating the quality of service. In the case of diabetes, this may include the stability of a blood glucose level in the body of the infused person.

Blood glucose levels or other controlled constituents of liquid in the body may be measured and input to the server system 54. The monitoring can be undertaken by conventional testing means with the infused person reporting the diagnostics through the two-way communication device 52. Alternatively, a sensor 60 may automatically generate a diagnostic signal indicative of the magnitude of a detected substance relevant to the infusion such as blood glucose. A similar radio chip and battery may be employed in associated with the sensor 60. Alternatively, the sensor 60 may communicate through the wireless link radio chip 39 of the controller 37 and even share the same energy source 38. The diagnostic may be employed by the controller 37 directly, such as through a table downloaded as commands to the controller 37. A variable of the infusion device would be amended in accordance with the look-up table responsive to a magnitude of the diagnostic input. Alternatively, the diagnostic may be transmitted to the two-way communication device where a downloaded program from the server system employs the diagnostic to generate commands to the controller 37.

In addition to the foregoing, the same infusion system can serve multiple patients, each with an infusion device 10 and a two-way communication device 52. In this case, the server system 54 includes access to a multiple number of files of operating instructions. With a full medical service, many patients each wearing an infusion device 10 and communicating through a two-way communication device 52, multiple control terminals accesses by multiple clinicians and multiple monitoring terminals 58 serving multiple payers can function from the same server system 54. Safeguards are provided to insure the electronic communication appropriately addresses the correct infusion device and correct file of operating instructions. Dual identification handshakes, passwords and the like are programmed into the system.

Figure 3:
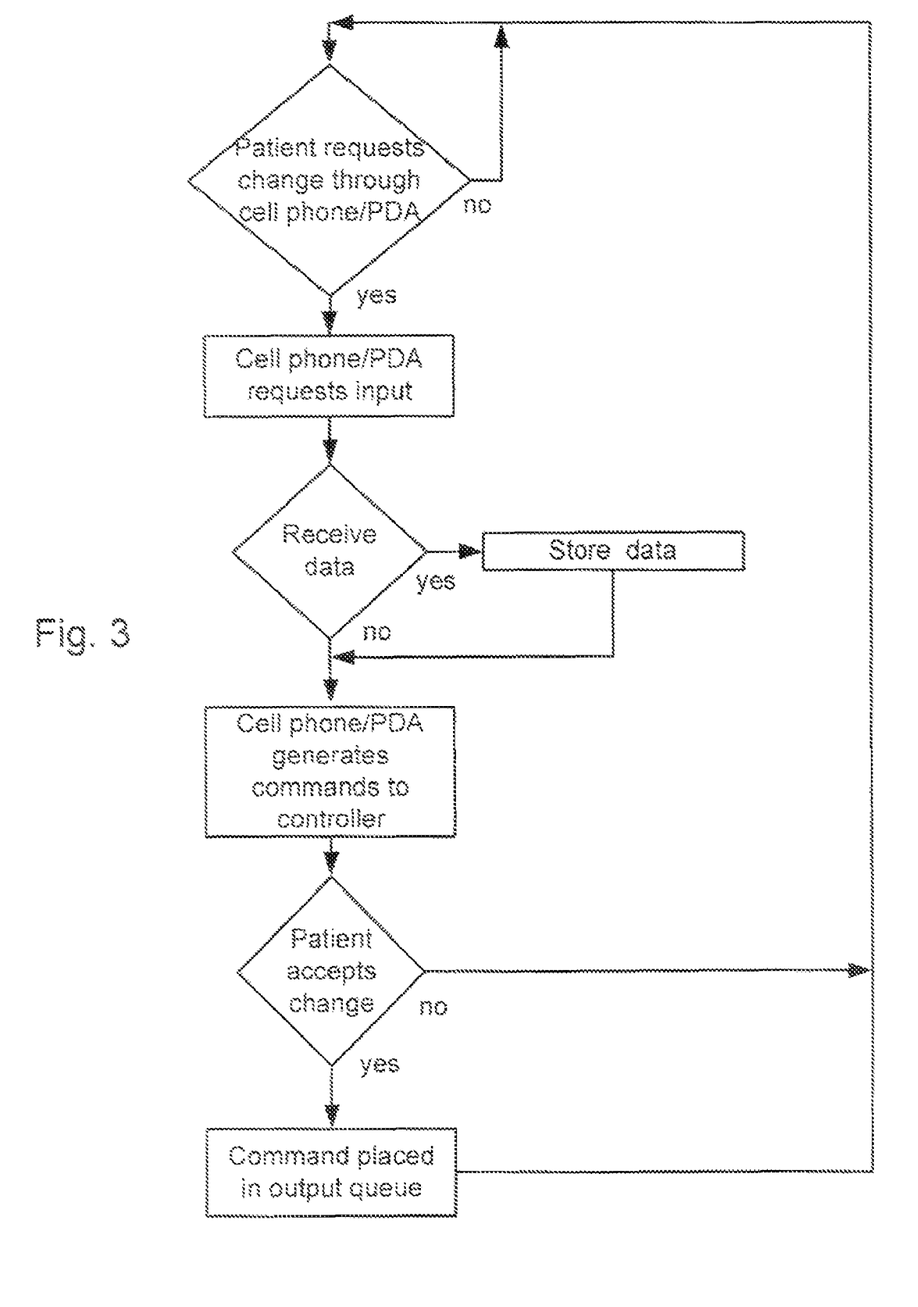
FIG. 3 is a logic diagram of the network system of FIG. 2 to serve a patient being infused.
Figure 4:
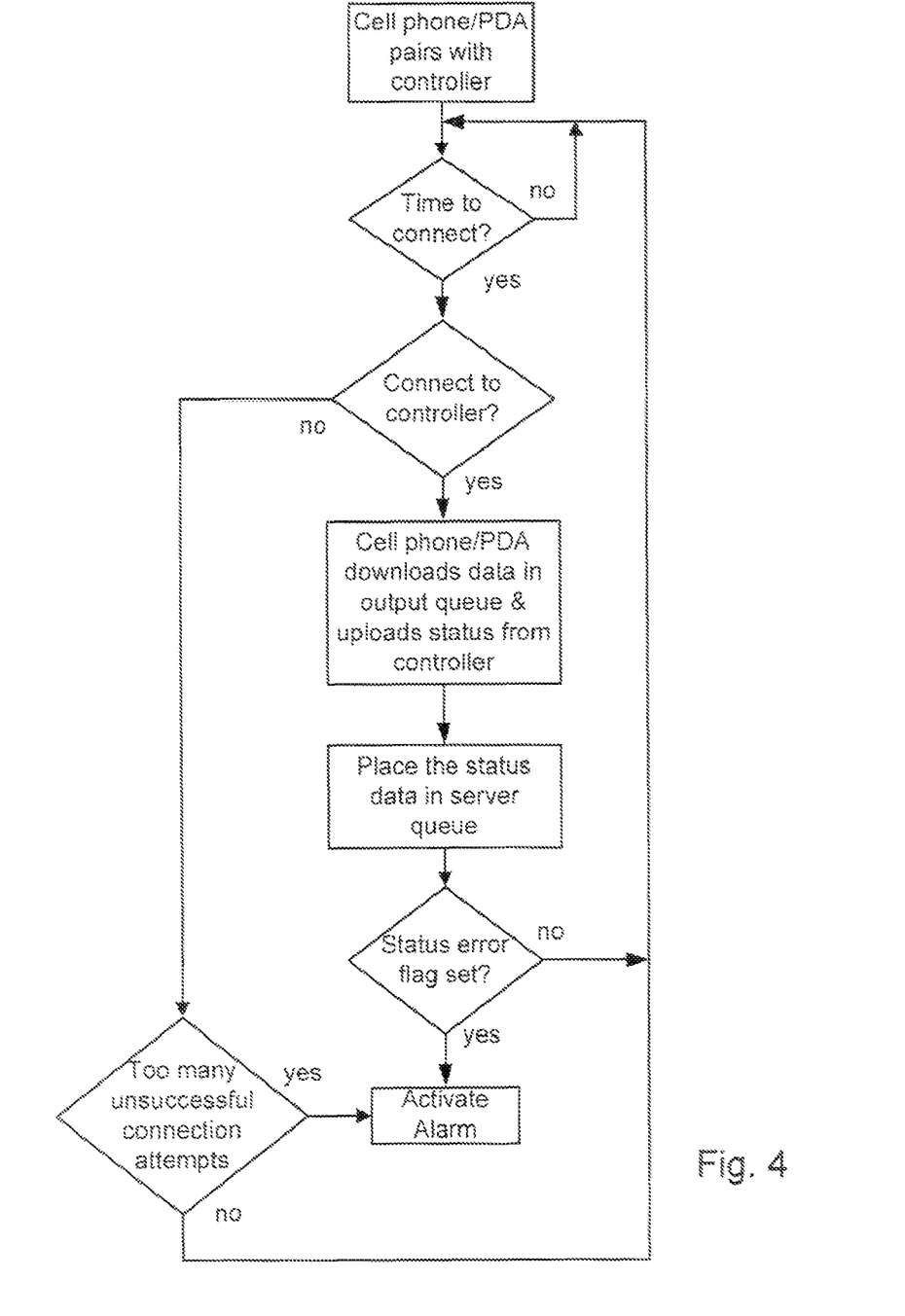
FIG. 4 is a logic diagram of the network system of FIG. 2 for a connection routine between a two-way communication device and an infusion device.
Figure 5:
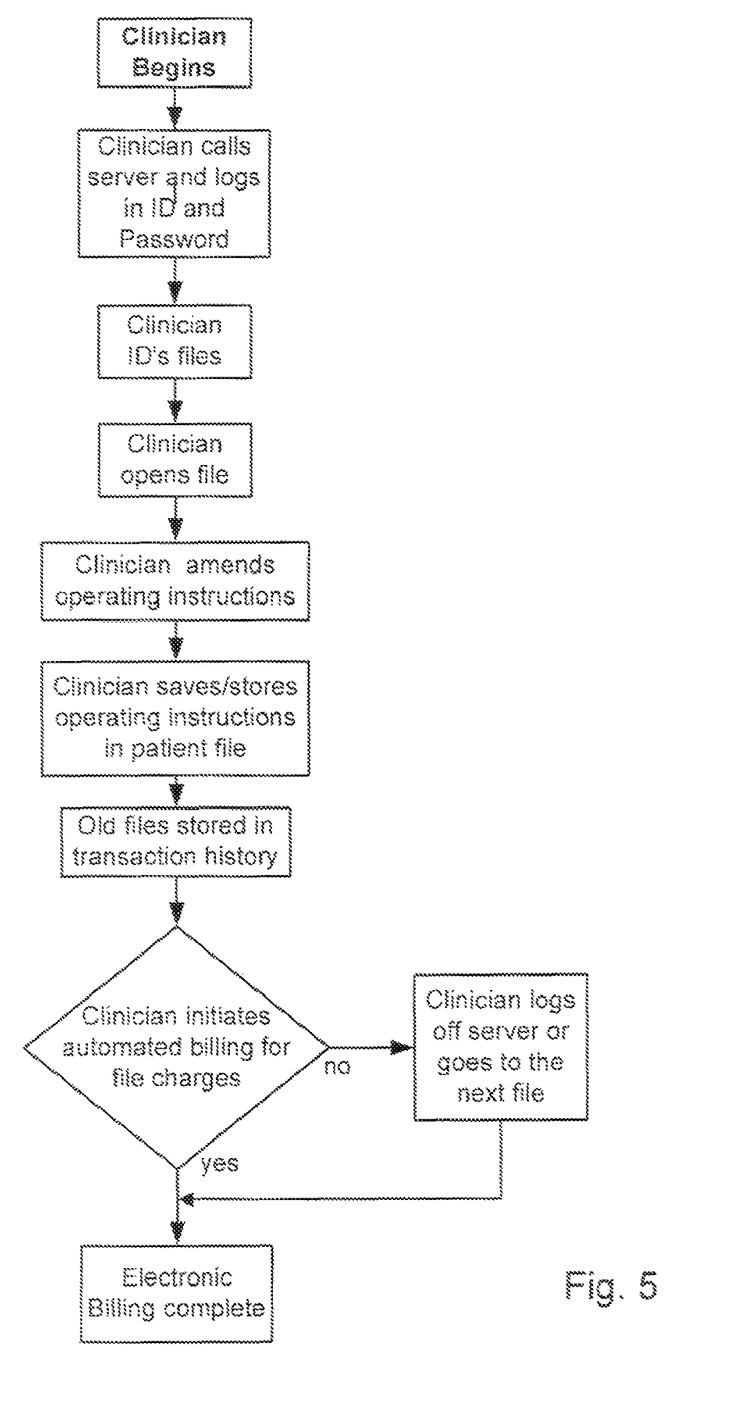
FIG. 5 is a logic diagram of the network system of FIG. 2 for clinician input.
Figure 6:
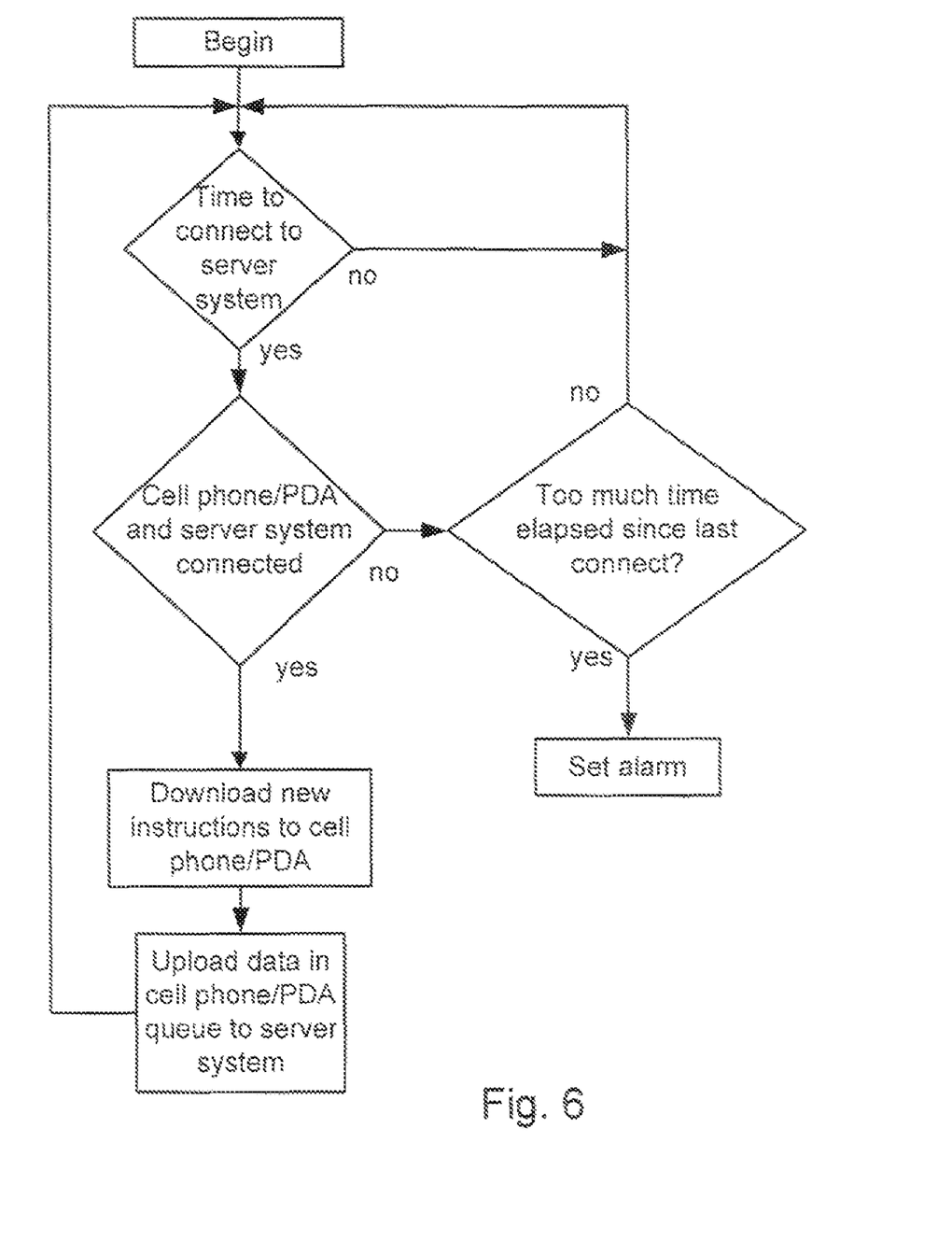
FIG. 6 is a logic diagram of the network system of FIG. 2 for a connection routine between the server system and the two-way communication device.
Figure 7:
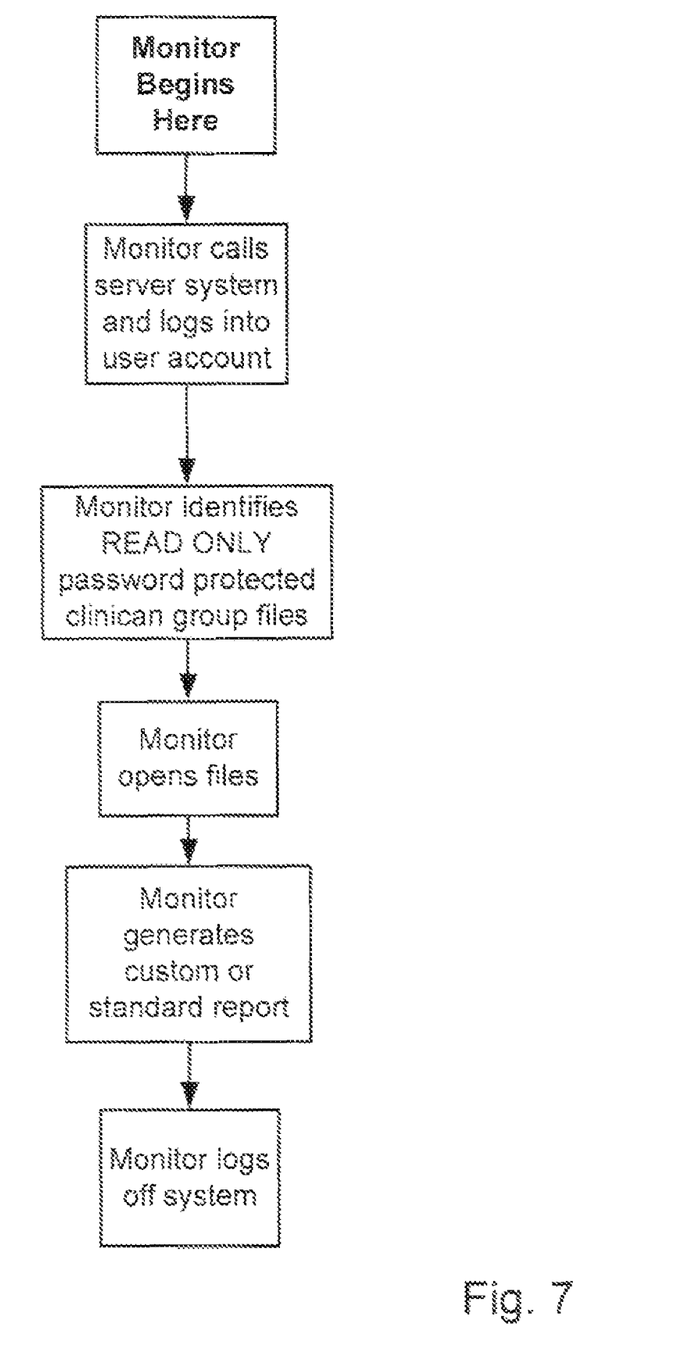
FIG. 7 is a logic diagram of the network system of FIG. 2 for payer monitoring.

Turning to system operation, a method for infusing liquid into a body is also presented. FIG. 3 illustrates communication logic with the patient interacting with the two-way communication device 52. FIG. 4 illustrate the logic steps for the two-way communication device 52 communicating with the controller 37. FIGS. 5 and 7 illustrate the logic steps for the control terminal and monitor terminal interfacing with the server system, respectively. FIG. 6 illustrates the logic steps for the server system 54 communicating with the two-way communication device 52.

In brief and looking to the Figures, the process of the patient interacting with the two-way communication device 52 begins with the patient inputting a request to the two-way communication device 52. In response, the two-way communication device 52 requests appropriate input. The input requested may be specifically responsive to the patient request or may follow certain repeated routines or both. The requested input may include blood glucose levels, anticipated carbohydrate intake, changes to settings, and the like. If the data is received, it is stored in the two-way communication device 52. In either event, the two-way communication device 52 generates appropriate commands as dictated by the program from the patient file, while commands are responsive to the patient request. The patient then accepts or rejects the change and, if accepted, the change is placed in the output queue. If rejected, the process is repeated.

The routine for the two-way communication device 52 to connect with a paired controller 37 is shown to include timing between the two. When the timing is correct, an attempt is made by the two-way communication device 52 with the controller 37 energized by synchronized timing to make contact. If the connection is made, the two-way communication device 52 downloads data from the output queue to the controller 37 and uploads status from the controller 37. If the status does not include an error flag, the process is recycled. If there are too many unsuccessful attempts to connect with the controller 37 or the status error flag is set, an alarm is activated. With a status error flag set in the controller 37, an alarm may be activated at the controller at that time. An alarm associated with the two-way communication device 52 and/or the server system 54 would be activated upon recognizing the status error flag or counting too many unsuccessful connection attempts.

The logic steps for use of the control terminal 56 is initiated by the clinician logging in. The appropriate file is retrieved and operating instructions are amended if the stored history, changes or new prescriptions are in place. The amendments are made and stored along with historical data. The clinician may further initiate automated billing for file charges and the process is complete.

For the communication between the server system 54 communicating with the two-way communication device 52, a time or incident initiation from either the two-way communication device 52 or the server system 54 initiates a connection. When connected, new and amended instructions are downloaded from the server system 54 to the two-way communication device 52 and data in the queue of the two-way communication device 52 is uploaded to the server system 54. When too much time is elapsed since the last connection, an alarm is set.

The operation of the monitor terminal 58 is initiated by a call to the server system 54. The monitor terminal 58 has read-only rights in the appropriate patient file accessed by the server system 54. The file is opened, a report is generated and the monitor terminal 58 logs off the system. With the monitor terminal 58 in the hands of a payer such as an insurance company, a bill can be generated based upon indication of clinician activity. Further, standard of care might also be evaluated if access is given to the historical data.

The programmable controller 37 is employed to control infusion into the body. To undertake that control, a file of information specific to the controller 37 is established and accessible to the server system 54. The server system 54 is associated with the extended area network preferably national or international in scope such as employs internet or cell phone technology. The server system 54 preferably has access to a great many files of information specific to controllers 37 to serve a large number of infusion patients. All such patients may be served over the extended area network to their individual two-way communication devices 52. From the server system 54, operating instructions including programming are transmitted over the extended area network to two-way communication devices 52. In the preferred embodiment above, the two-way communication devices 52 are Java-enabled cell phones with the extended area network being a cellular or satellite telephone network.

The creation or modification of information specific to a patient infusion device 10 is accomplished through the control terminal 56 by amending the updatable file of operating instructions. This function is illustrated in the logic diagram of FIG. 5. The control terminal is typically operated by a clinician remote from the server system. The rules of control for the controller 37 are established within the file of operating instructions. Such rules, as determined by the clinician, may include a set basal rate or a range of permitted basal rates. Such settings may be arranged on the basis of periods of the day to track common changes in infusion needs as more specifically fine tuned for each individual. The file further contains rules for bolus administration. Limits and specific values may be incorporated into the file of information specific to the controller for the specific patient, which may include rules responsive to estimated carbohydrate intake. The file can also keep track of the history of activity by the clinician for billing purposes. The file of updatable information also receives input from the two-way communication device 52, which principally historical or indicative of device status.

With the use of a programmable two-way communication device 52, the server system 54 may download programming including operating instructions at regular or requested intervals to the two-way communication device 52. This function is illustrated in the logic diagram of FIG. 3. Such instructions may be principally programming specific to the patient as dictated by the clinician. The programming in the two-way communication device 52 is appropriately updated at a frequency which maintains adequate currency from the server system 54. The routine may include having the patient query the server system 54 each time the patient makes a request. The patient, or caregiver with the patient, may repeatedly interact with the two-way communication device 52 to request basal rate changes and boluses between changes in the basic program input from the server system 54 to the two-way communication device 52. Such independent operation is of particular benefit when network access for each the server system 54 is unavailable.

The patient input includes secure identification and may be undertaken using keypad input or voice communication to the programmable cell phone 52 or to the other devices discussed above. The two-way communication device 52 can then prompt, orally or visually, for the necessary input. Such input appropriately would include the estimated amount of carbohydrates in the case of diabetics which have just been ingested or are to be ingested for a bolus. Periodically current blood glucose level can be demanded of or voluntarily submitted by the patient to be entered manually from patient testing or automatically on a periodic basis from a sensor 60. These functions are seen in the logic diagram of FIG. 3. The degree of control afforded the patient is also determined in the programming by the clinician.

The requested basal rate changes and bolus requests input to the two-way communication device 52 are transmitted as program commands. The commands are sent through the wireless link 39 to the programmable controller 37. The commands for implementation are maintained within the boundaries of discretion dictated by the operating instructions to the two-way communication device 52 from the patient file accessible by the server system 54.

Currency is also maintained in the patient file accessible to the server system 54 by return from the two-way communication device 52 of data regarding the history of requests, rate changes, boluses administered, recorded changes in constituent fluid status, system and component status and other possible input such as demographics or diabetes centers. Such information is useful to the clinician for subsequent treatment and to any analysis of treatment efficacy. This input from the two-way communication device 52 may follow some period of operation independent of the server system 54 or be timed to more closely monitor patients in unstable circumstances. The server system 54 can also generate automatic alerts to clinicians when malfunctions are sensed or boundary values are exceeded as discussed below. The system is designed to check periodically as well as be connected when requests or changes are made.

The monitoring of care of a patient and efficacy of the treatment can be undertaken from analysis of the patient file from any authorized terminal. This function is illustrated in the logic diagram of FIG. 6. The monitoring terminal 58 is provided with network access. Such access may be limited to information retrieval and may further be limited to specific information. Use of the monitoring terminal 58 may be employed for generating payments to providers for accumulating activity of the clinician such as monitoring constituents of liquid in the body, amending basal rate and bolus authorizations and the like. The transmission of information prompting billing may occur through generation of a communication by the clinician or by monitoring by the payer. The payer may then generate payments to the service providers consistent with such activity. Additionally, the monitoring function through the monitoring terminal 58 may include oversight of the monitoring effectiveness and quality of control over the controlled constituents of liquid in the patient. Through such oversight functions, risk factors can be accessed. The inability to control glucose levels in a diabetic patient, for example, would signal an increased level of risk of complications.

Communication between the controller and the two-way communication device is arranged to conserve battery power in the infusion device. Rather than have the wireless link prepared to receive communication from the two-way communication device at any time, the two-way communication device and controller sync clocks each time they do communicate. Further, a time interval, say five minutes, is set when the controller is to turn on the wireless link and the two-way communication device sends a signal to the controller. The signal may be the initiation of a change in infusion rate and/or sequence or communication of infusion device status and a further sync of the clocks for another period, thereby setting up scheduled data shuttles. The logic steps for this operation are illustrated in FIG. 4.

When the user requests a change or the server downloads a change to the two-way communication device under the battery conservation scheme, the two-way communication device is scheduled for a download to the controller. At the appointed interval, the controller switches on and the two-way communication device transmits the change to the controller. Where control is time critical, a short time interval can be used for the scheduled data shuttles.

The schedule may be used to monitor and signal concern. If the communication device fails to establish a connection to the controller through the wireless link after a preprogrammed number of tries, the two-way communication device will alert the user through an audio or vibrational alarm as the infusion device has either malfunctioned, including having a dead battery, or the device is out of range of the two-way communication device.

A further failsafe mechanism can be implemented by requiring the two-way communication device to signal the server on a regular basis that communication to the infusion device is maintained and that an error-free status byte has been received. If the server does not receive this information, either the infusion device has failed or is out of range of the two-way communication device or the two-way communication device has failed or is out of range of any transfer station. The server can then send an alert such as by calling an emergency number.

Thus, an improved method and apparatus for the infusion of liquid to a body is disclosed. While embodiments and applications of this invention have been shown and described, it would be apparent to those skilled in the art that many more modifications are possible without departing from the inventive concepts herein. The invention, therefore it not to be restricted except in the spirit of the appended claims.

What is claimed is:

1. A device for infusing liquid to a body, comprising
  a single use disposable assembly including a source of infusion fluid, a delivery port to the body, and a pump coupled between the source of infusion fluid and the delivery port and having a pump chamber, a diaphragm retained about the periphery thereof to the disposable assembly and a piston centrally located on one side of the diaphragm, the piston extending to the pump chamber to vary the chamber volume;
  a multiuse assembly separable from the single use disposable assembly and including a piezoelectric arm retained at one end in the multiuse assembly and having an actuator member moving with the piezoelectric arm extending from the multiuse assembly to the other side of the diaphragm at the piston and a controller capable of programmable infusion rate and time sequences.

2. The device of claim 1, the diaphragm always being in radial tension to define a restoring force to bias the actuator member toward one end of the stroke of the actuator member.

3. The device of claim 1 further comprising
  a battery in the multiuse assembly.

4. The device of claim 1, the source of source of infusion fluid being a reservoir.

5. The device of claim 1 further comprising
a system including a two-way communication device having a transceiver capable of wireless communication with the controller using a local area communication standard and capable of wireless communication through an extended area network.

6. The device of claim 5, the system further including a server system capable of communication with the two-way communication device through the extended area network and having access to a file of updatable information specific to the controller, the two-way communication device being programmable by the server system over the extended area network.

7. The device of claim 5, the system further including a sensor capable of generating a diagnostic signal and being in communication with the controller or the two-way communication device, the signal being incorporated into commands for operation of the controller.

8. A device for infusing liquid to a body, comprising
a single use disposable assembly including a source of infusion fluid, a delivery port to the body, and a pump coupled between the source of infusion fluid and the delivery port and having a pump chamber including a cylinder, a diaphragm retained about the periphery thereof to the disposable assembly and a piston integrally located on one side of the diaphragm, the piston extending to the cylinder to vary the chamber volume;
a multiuse assembly separable from the single use disposable assembly and including an actuator member extending from the multiuse assembly to contact with the other side of the diaphragm at the piston and a controller capable of programmable infusion rate and time sequences to move the actuator.

9. A device for infusing liquid to a body, comprising
a single use disposable assembly including a source of infusion fluid, a delivery port to the body, and a pump coupled between the source of infusion fluid and the delivery port and having a pump chamber including a cylinder, a diaphragm retained about the periphery thereof to the disposable assembly and a piston integrally located on one side of the diaphragm, the piston extending to the cylinder to vary the chamber volume;
a multiuse assembly separable from the single use disposable assembly and including an actuator member extending from the multiuse assembly to contact the other side of the diaphragm at the piston and to impose radial tension on the diaphragm with the single use disposable assembly and the multiuse assembly engaged and a controller capable of programmable infusion rate and time sequences to move the actuator.

* * * * *